United States Patent
Arrowsmith et al.

(10) Patent No.: US 8,999,903 B2
(45) Date of Patent: Apr. 7, 2015

(54) ADDITIVES AND LUBRICATING OIL COMPOSITIONS CONTAINING SAME

(75) Inventors: Stephen Arrowsmith, Didcot (GB); Christopher J. Booth, Reading (GB); Aubrey L. Burrows, Diss (GB); Paul Wilson, Abingdon (GB); Neal J. Milne, Ramsbury (GB); Lin Wangkan, Bridgewater, NJ (US); Jacob Emert, Brooklyn, NY (US); Laurent Chambard, Englewood, NJ (US)

(73) Assignee: Infineum International Limited (GB)

( * ) Notice: Subject to any disclaimer, the term of this patent is extended or adjusted under 35 U.S.C. 154(b) by 385 days.

(21) Appl. No.: 12/602,204

(22) PCT Filed: Jun. 6, 2008

(86) PCT No.: PCT/US2008/066026
§ 371 (c)(1),
(2), (4) Date: Mar. 22, 2010

(87) PCT Pub. No.: WO2008/154334
PCT Pub. Date: Dec. 18, 2008

(65) Prior Publication Data
US 2010/0173811 A1    Jul. 8, 2010

(30) Foreign Application Priority Data

Jun. 8, 2007   (EP) .................................... 07109917

(51) Int. Cl.
| | | |
|---|---|---|
| *C10M 169/04* | (2006.01) | |
| *C10M 133/12* | (2006.01) | |
| *C10M 141/08* | (2006.01) | |
| *C07C 209/68* | (2006.01) | |
| *C09K 15/08* | (2006.01) | |
| *C09K 15/18* | (2006.01) | |

(52) U.S. Cl.
CPC .............. *C07C 209/68* (2013.01); *C09K 15/08* (2013.01); *C09K 15/18* (2013.01); *C10M 133/12* (2013.01); *C10M 2207/026* (2013.01); *C10M 2215/064* (2013.01); *C10M 2215/28* (2013.01); *C10N 2220/021* (2013.01); *C10N 2220/028* (2013.01); *C10N 2220/029* (2013.01); *C10N 2220/033* (2013.01); *C10N 2230/02* (2013.01); *C10N 2230/04* (2013.01); *C10N 2230/10* (2013.01); *C10N 2240/10* (2013.01)

(58) Field of Classification Search
CPC ...... C07C 209/68; C09K 15/08; C09K 15/18; C10M 2215/064; C10M 2215/28; C10M 159/24; C10M 135/30; C10M 2205/024; C10M 2205/0245; C10M 2205/0265; C10M 2205/063; C10M 2207/00; C10M 2207/04; C10M 2207/046; C10M 2215/062; C10M 2215/12; C10M 2215/122; C10M 2215/224; C10M 2219/02; C10M 2219/024; C10M 2219/042; C10M 2219/082; C10N 2220/033; C10N 2220/021; C10N 2220/029; C10N 2220/028; C10N 2230/02; C10N 2230/04; C10N 2230/10; C10N 2240/10; C10N 2240/04; C10N 2240/104; C10N 2240/106; C10N 2240/102; C10N 2240/103; C10N 2240/30; C10N 2240/50; C10N 2240/52; C10N 2240/54; C10N 2240/56; C10N 2240/58; C10N 2240/60; C10N 2240/66
USPC ........................... 508/287, 563, 556; 564/409
See application file for complete search history.

(56) References Cited

U.S. PATENT DOCUMENTS

| 3,284,504 | A | * | 11/1966 | Rosenwald | .................... | 564/433 |
| 5,214,211 | A | * | 5/1993 | Kurek et al. | .................. | 564/409 |
| 7,145,038 | B1 | * | 12/2006 | Hobbs | ........................... | 564/409 |

FOREIGN PATENT DOCUMENTS

| EP | 0416914 A1 | * | 9/1990 |
| EP | 0416914 A1 | | 3/1991 |

OTHER PUBLICATIONS

Vincent J. Gatto et al., "Redesigning Alkylated Diphenylamine Antioxidants for Modern Lubricants", Lubrication Science 2007; 19: 25-40, XP-002454737.

* cited by examiner

*Primary Examiner* — James Goloboy
*Assistant Examiner* — Latosha Hines

(57) ABSTRACT

Para-alkylated substituted diphenylamines are made by catalytically alkylating diphenylamine with a branched-chain alkene, such as propene, oligomer mixture in which the oligomer present in the greatest percentage has 15-24 carbon atoms. The alkylated diphenylamines are useful crankcase lubricant additives such as for reducing piston deposits and engine sludge.

2 Claims, No Drawings

ADDITIVES AND LUBRICATING OIL COMPOSITIONS CONTAINING SAME

FIELD OF THE INVENTION

This invention relates to para-alkylated diphenylamines, useful for example as lubricant additives, and their preparation.

BACKGROUND OF THE INVENTION

Alkylated diphenylamines are well-known anti-oxidants such as for use as additive components in lubricating oil compositions (or lubricants) for lubricating the crankcase of spark-ignited or compression-ignited internal combustion engines. The art describes making them by catalytically alkylating diphenylamine by means of an alkene (or alkylene) alkylating agent. Among the alkylating agents described in the art there are mentioned oligomers of propene, also referred to as propylene.

U.S. Pat. No. 5,214,211 mentions use of propylene oligomers to alkylate diphenylamine.

EP-A-0416 914 describes p,p'-dialkyldiphenylamine with branched alkyl groups having 12 or 15 carbon atoms, derived from oligomers of propylene.

U.S. Pat. No. 6,315,925 A describes nonylated diphenylamines using tripropylene, a C9 olefin, as the nonylating agent. Nonylated diphenylamines are used commercially as anti-oxidants in crankcase lubricants; examples include Irganox® L57 and Naugalube® 640.

US 2004/0211113 A1 describes producing alkylated diphenylamines by alkylating a diphenylamine with a mixture of oligomers of propylene, but does not identify the oligomers that may be used.

US 2006/0276677 A1 describes alkylating diphenylamine with an alkylating agent in the form of an alkylene, or mixture of isomeric olefins, having 4 to 28 carbon atoms. The use of propylene tetramer, a C12 olefin, as alkylating agent is specifically exemplified.

Gatto et al, in a paper entitled "Redesigning alkylated diphenylamine antioxidants for modern lubricants" and published in Lubrication Science 2007; 19: 25-40 report tests on $C_9$ and propylene tetramer $C_{12}$ alkylated diphenylamines and conclude that data were presented showing that high molecular weight diphenylamines are less effective on an equal weight basis than the other structures examined.

A problem in the art is to provide alkylated diphenylamines, derived from propene oligomers, that have surprisingly advantageous properties as lubricant additives particularly in respect of piston deposits and engine sludge, as well as having satisfactory effectiveness as lubricant anti-oxidants. The art makes no mention of alkylated diphenylamines having piston deposit reduction properties.

SUMMARY OF THE INVENTION

This invention surprisingly meets the problem in the art, as evidenced by the data herein, by use of defined alkylate diphenylamines.

Thus, in a first aspect, the invention comprises a method of preparing a para-alkyl-substituted diphenylamine comprising catalytically alkylating diphenylamine with an alkylating agent in the form of a mixture of branched-chain alkene oligomers, wherein the oligomer that is present in the greatest percentage has a number of carbon atoms that is in the range of 15 to 24, oligomers having 9 or fewer carbon atoms constitute 25% or less of the mixture, and oligomers having from 24 to 36 carbon atoms constitute 50% or less of the mixture, all percentages being area/area as measured chromatographically.

In a second aspect, the invention comprises a composition comprising or made by admixing an oil of lubricating viscosity; and
(A) as an additive component, a para-alkyl-substituted diphenylamine wherein:
  (i) the alkyl group or groups are branched, are derived from branched-chain alkene oligomers and the alkyl group present in the greatest percentage has from 15 to 45, preferably 15, carbon atoms, 25% or less of the alkyl groups having 9 or fewer carbon atoms and 25% or less of the alkyl groups having 45 or more carbon atoms;
  (ii) 25% or less of the substituted diphenylamine is tri-alkyl-substituted; and
  (iii) 10% or less of the substituted diphenylamine is ortho-substituted,
wherein all percentages are area/area as measured chromatographically.

In a third aspect, the invention comprises a composition comprising or made by admixing:
(A) an oil of lubricating viscosity; and
(B) as an additive component, a para-alkyl-substituted diphenylamine obtained or obtainable by catalytically alkylating diphenylamine with an alkylating agent in the form of a mixture of branched-chain alkene oligomers which mixture contains more propene pentamer by mass than any other propene oligomer.

In a fourth aspect, the invention comprises a crankcase lubricating oil composition comprising an oil of lubricating viscosity in a major amount and, in respective minor amounts,
(A) as an additive component, a para-alkyl-substituted diphenylamine wherein:
  (i) the alkyl group or groups are branched, are derived from branched-chain alkene oligomers and the alkyl group present in the greatest percentage has from 12 to 45, preferably 12 or 15, carbon atoms, 25% or less of the alkyl groups having 9 or fewer carbon atoms and 25% or less of the alkyl groups having 45 or more carbon atoms;
  (ii) 25% or less of the substituted diphenylamine is tri-alkyl-substituted; and
  (iii) 10% or less of the substituted diphenylamine is ortho-substituted; and
(B) one or more additives other than (A) selected from ashless dispersants, metal detergents, corrosion inhibitors, metal dihydrocarbyl dithiophosphates, antioxidants, pour-point depressants, friction modifiers, anti-foam agents and viscosity modifiers,
the composition having greater than 3.5 average weighted piston deposits merits measured according to the Sequence III G Engine Oil Certification Test (ASTM D7320) and/or greater than 7.8 average sludge merits measured according to the Sequence VG Engine Oil Certification Test (ASTM D5302).

In a fifth aspect, the invention comprises a method of lubricating the crankcase of an internal combustion engine using a lubricating oil composition according to the fourth aspect of the invention.

In a sixth aspect, the invention comprises a 0WX or 5WX crankcase lubricating oil composition where X is 10, 20, 30, 40 or 50 comprising an oil of lubricating viscosity in a major amount and, in respective minor amounts,
(A) as an additive component, a para-alkyl-substituted diphenylamine wherein:

(i) the alkyl group or groups are branched, are derived from propene oligomers and the alkyl group present in the greatest percentage has from 12 to 45, preferably 12 or 15, carbon atoms, 25% or less of the alkyl groups having 9 or fewer carbon atoms and 25% or less of the alkyl groups having 45 or more carbon atoms;

(ii) 25% or less of the substituted diphenylamine is tri-alkyl-substituted; and (iii) 10% or less of the substituted diphenylamine is ortho-substituted; and (B) one or more additives other than (A) selected from ashless dispersants, metal detergents, corrosion inhibitors, metal dihydrocarbyl dithiophosphates, antioxidants, pour-point depressants, friction modifiers, antifoam agents and viscosity modifiers.

In a seventh aspect, the invention comprises a method of improving piston cleanliness, as measured by average weighted piston deposits according to the Sequence III G Engine Oil Certification Test (ASTM D 7320), when lubricating the crankcase of an internal combustion engine with a lubricating oil composition containing a minor amount of an additive component (A) as defined in the fourth aspect of the invention, in comparison with an otherwise identical lubricating oil composition that contains a para-nonyl-substituted diphenylamine in place of component (A).

In all aspects of the invention, the branched-chain alkene oligomers are preferably branched-chain propene oligomers.

In this specification, the following words and expressions, if and when used, have the meanings ascribed below:

"active ingredient" or "(a.i.)" refers to additive material that is not diluent or solvent;

"comprising" or any cognate word specifies the presence of stated features, steps, or integers or components, but does not preclude the presence or addition of one or more other features, steps, integers, components or groups thereof; the expressions "consists of" or "consists essentially of" or cognates may be embraced within "comprises" or cognates, wherein "consists essentially of" permits inclusion of substances not materially affecting the characteristics of the composition to which it applies;

"major amount" means in excess of 50 mass % of a composition;

"minor amount" means less than 50 mass % of a composition;

"TBN" means total base number as measured by ASTM D2896.

Furthermore in this specification:

"phosphorus content" is as measured by ASTM D5185;

"sulfated ash content" is as measured by ASTM D874;

"sulphur content" is as measured by ASTM D2622;

"kV$_{100}$" means kinematic viscosity at 100° C. as measured by ASTM D445.

Also, it will be understood that various components used, essential as well as optimal and customary, may react under conditions of formulation, storage or use and that the invention also provides the product obtainable or obtained as a result of any such reaction.

Further, it is understood that any upper and lower quantity, range and ratio limits set forth herein may be independently combined.

DETAILED DESCRIPTION OF THE INVENTION

The features of the invention relating, where appropriate, to each and all aspects of the invention, will now be described in more detail as follows:

Para-Alkyl-Substituted Diphenylamines

The alkylated diphenylamines of the invention are, in practice, mixtures arising from the presence of isomeric forms of the alkyl substituents, variation in the number of alkyl substituents on each diphenylamine moiety and variation in the position of the substitution on each diphenylamine moiety. Also, the mixtures may include material that carries no para-alkyl substituent such as unreacted (unsubstituted) diphenylamine and material that is substituted in one or two ortho positions only, the latter being o'-substituted.

The mixtures of the invention contain, however, a major proportion, or all, material that is substituted in one or both para (i.e. 4 and/or 4') positions. Material that is para-substituted in one position only is referred to as mono-substituted material; material that is para-substituted in both positions only is referred to as disubstituted material. The mixtures of the invention may further include small quantities of tri-substituted material, i.e. substituted in both para positions and one ortho position, and unreacted diphenylamine. The presence of tri-substituted material is usually regarded as undesirable for lubricant additive performance.

As indicated, the mixtures may include other ortho substituted material. This may include mono-ortho, di-ortho and ortho-para substituted material. Such material may, in some cases, constitute up to less than 10, such as up to 5, % of the mixture. Their presence, however, is not considered to assist lubricant additive performance.

Importantly, para (mono and/or di) substitution should predominate in the mixtures of the invention. The ratio of mono:di material can be in the range of 100:0 to 0:100 such as 90:10 or 80:20 or 70:30 to 30:70. Preferably, the ratio of mono:di material exceeds 50:50 such as exceeding 60:40. In one embodiment, the alkylated diphenylamine consists of material that is alkyl-substituted in the 4-position only.

When the alkylating agent is a mixture of propene oligomers, the alkyl groups may also include those with a number of carbon atoms that is not a multiple of three. This may arise from the presence of cracked propane oligomers in the alkylating agent used in preparing the substituted diphenylamines of this invention.

As examples of the substituted diphenylamines of this invention, there may be mentioned those wherein the alkyl group present in the largest percentage has either 15 or 30 carbon atoms. Where the alkyl group present in the largest percentage has 15 carbon atoms, alkyl groups with 15 carbon atoms may constitute more than 50% of all alkyl groups present, though in other cases they may constitute less than 50% of all alkyl groups present.

There may be further mentioned diphenylamines of the invention wherein 10% or less of the alkyl groups have 9 or fewer carbon atoms and 10% or less of the alkyl groups have 45 or more carbon atoms.

The following should also be noted: 95 or more, such as 97 or more, % of the substituent alkyl groups, as measured area/area chromatographically, may have more than 9 carbon atoms; also, the average molecular weight of the alkyl groups may be in the range of 140 to 340, such as 140 to 300.

Preparative Method

The alkylation is carried out catalytically such as and preferably by using a Lewis acid catalysts for the Friedel-Crafts alkylation of aromatic compounds. Examples include AlCl$_3$ and BF$_3$ and their derivatives.

The catalyst used may also be a clay catalyst such as known in the art. Preferred are sub-bentonites or bentonites which consist predominantly of the clay mineral montmorillonite. Clays may be used in amounts of 1 to 60, preferably 2 to 20, mass % based on the mass of reactant diphenylamine.

Commercially-available clays include the following, identified by their respective trade marks: Filtrol, Retrol, Fulcat, Fulmont and Katalysator. They may include acid-activated or acid-leached clays.

Clays are aluminosilicates: aluminium III cations are bonded to an octahedral arrangement of oxygen anions. Repetition of $MO_6$ units in two dimensions forms an octahedral layer and, likewise, a tetrahedral layer is formed from $SiO_4$ units. Clays are classified according to the relative number of tetrahedral and octahedral layers, montmorillonite (mentioned above) having an octahedral layer sandwiched between two tetrahedral layers.

Typically, the alkylation is carried out at a pressure of from atmospheric pressure to 10 bar and at a temperature of from 120 to 190° C. The ratio (weight:weight) of alkylating agent to diphenylamine may, for example, be in the range of 1.5:1 to 5:1, and the catalyst preferably be present in the range of 1 to 10 percent by weight, based on the weight of reactant diphenylamine. Suitably, the alkylation may be carried out in an inert atmosphere.

As an example of the alkylating agent there may be mentioned a mixture comprising $C_{12}$, $C_{15}$, $C_{18}$ and $C_{21}$ propene oligomers which contains more by mass of the $C_{15}$ oligomer than of any of the $C_{12}$, $C_{18}$ and $C_{21}$ oligomers individually. Such mixtures are available commercially, one being "Pentamer K" marketed by Chevron Oronite, given the name Propylene Pentamer and described as a "highly branched, predominately $C_{15}$ mono-olefin".

The mole ratio of alkylating agent to diphenylamine may be in the range of 1:3 to 6:1, preferably 1:3 to 1.5:1, or 2:1 to 6:1, preferably 4:1. More preferred is 1:3 to 0.8:1.

The alkylating agent used is or may be a mixture in more than one sense. Firstly, it may contain oligomers of more than one carbon number. Secondly, an oligomer of specified carbon number may be present in more than one isomeric form. References in this specification to an oligomer having a specified number of carbon atoms is taken to embrace different isomeric forms thereof. The word "oligomer" means, in this specification, any polymer having a number of carbon atoms stated therein, some of which, because they have a higher number of carbon atoms, may in different contexts, be termed "polymers".

In a preferred alkylating agent, oligomers having 9 or fewer carbon atoms and oligomers having 24 or more carbon atoms together constitute 10% or less of the mixture. The alkylating agent may consist of a mixture of branched-chain $C_{15}$ propene oligomers.

Oil of Lubricating Viscosity (A)

The oil of lubricating viscosity (sometimes referred to as "base stock" or "base oil") is the primary liquid constituent of a lubricant into which additives and possible other oils are blended, for example to produce a final lubricant (or lubricant composition).

A base oil is useful for making concentrates as well as for making lubricating oil compositions therefrom, and may be selected from natural (vegetable, animal or mineral) and synthetic lubricating oils and mixtures thereof. It may range in viscosity from light distillate mineral oils to heavy lubricating oils such as gas engine oil, mineral lubricating oil, motor vehicle oil and heavy duty diesel oil. Generally the viscosity of the oil ranges from 2 to 30, especially 5 to 20, $mm^2s^{-1}$ at 100° C.

Natural oils include animal and vegetable oils (e.g. castor and lard oil), liquid petroleum oils and hydrorefined, solvent-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils such as polymerized and interpolymerized olefins (e.g. polybutylenes, polypropylenes, propylene-isobutylene copolymers, chlorinated polybutylenes, poly(1-hexenes), poly(1-octenes), poly(1-decenes)); alkylbenzenes (e.g. dodecylbenzenes, tetradecylbenzenes, dinonylbenzenes, di(2-ethylhexyl)benzenes); polyphenols (e.g. biphenyls, terphenyls, alkylated polyphenols); and alkylated diphenyl ethers and alkylated diphenyl sulfides and the derivatives, analogues and homologues thereof.

Another suitable class of synthetic lubricating oil comprises esters of dicarboxylic acids (e.g. phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, alkenyl malonic acids) with a variety of alcohols (e.g. butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols, and polyol ethers such as neopentyl glycol, trimethylolpropane, pentaerythritol, dipentaerythritol and tripentaerythritol.

Unrefined, refined and re-refined oils can be used in the compositions of the present invention. Unrefined oils are those obtained directly from a natural or synthetic source without further purification. For example, a shale oil obtained directly from retorting operations, a petroleum oil obtained directly from distillation or ester oil obtained directly from an esterification process and used without further treatment would be unrefined oil. Refined oils are similar to unrefined oils except that they have been further treated in one or more purification steps to improve one or more properties. Many such purification techniques, such as distillation, solvent extraction, acid or base extraction, filtration and percolation are known to those skilled in the art. Re-refined oils are obtained by processes similar to those used to obtain refined oils from refined oils that have already been used. Such re-refined oils are also known as reclaimed or reprocessed oils and are often additionally processed by techniques for treating spent additive and oil breakdown products.

Other examples of base oil are gas-to-liquid ("GTL") base oils, i.e. the base oil may be an oil derived from Fischer-Tropsch synthesised hydrocarbons made from synthesis gas containing $H_2$ and CO using a Fischer-Tropsch catalyst. These hydrocarbons typically require further processing to make them useful as base oils. For example, they may, by methods known in the art, need to be hydroisomerized; hydrocracked and hydroisomerized; dewaxed; or hydroisomerized and dewaxed.

The oil of lubricating viscosity may comprise a Group I, Group II or Group III, base stock or base oil blends of the aforementioned base stocks. Preferably, the oil of lubricating viscosity is a Group II or Group III base stock, or a mixture thereof, or a mixture of a Group I base stock and one or more a Group II and Group III. Preferably, a major amount of the oil of lubricating viscosity is a Group II, Group III, Group IV or Group V base stock, or a mixture thereof. The base stock, or base stock blend preferably has a saturate content of at least 65%, more preferably at least 75%, such as at least 85%. Most preferably, the base stock, or base stock blend, has a saturate content of greater than 90%. Preferably, the oil or oil blend will have a sulfur content of less than 1%, preferably less than 0.6%, most preferably less than 0.4%, by weight.

Preferably the volatility of the oil or oil blend, as measured by the Noack volatility test (ASTM D5880), is less than or equal to 30%, preferably less than or equal to 25%, more preferably less than or equal to 20%, most preferably less than or equal 16%. Preferably, the viscosity index (VI) of the oil or oil blend is at least 85, preferably at least 100, most preferably from about 105 to 140.

Definitions for the base stocks and base oils in this invention are the same as in API EOLCS 1509, which categorizes base stocks as follows:
 a) Group I base stocks contain less than 90 percent saturates and/or greater than 0.03 percent sulfur and have a viscosity index greater than or equal to 80 and less than 120 using the test methods specified in Table 1.
 b) Group II base stocks contain greater than or equal to 90 percent saturates and less than or equal to 0.03 percent sulfur and have a viscosity index greater than or equal to 80 and less than 120 using the test methods specified in Table 1.
 c) Group III base stocks contain greater than or equal to 90 percent saturates and less than or equal to 0.03 percent sulfur and have a viscosity index greater than or equal to 120 using the test methods specified in Table 1.
 d) Group IV base stocks are polyalphaolefins (PAO).
 e) Group V base stocks include all other base stocks not included in Group I, II, III, or IV.

TABLE I

Analytical Methods for Base Stock

| Property | Test Method |
|---|---|
| Saturates | ASTM D 2007 |
| Viscosity Index | ASTM D 2270 |
| Sulfur | ASTM D 2622 |
|  | ASTM D 4294 |
|  | ASTM D 4927 |
|  | ASTM D 3120 |

The oil of lubricating viscosity may be present in a concentrate-foaming amount (e.g., from 30 to 70, such as 40 to 60, mass %) so that the composition is in the form of a concentrate containing for example 1 to 90, such as 10 to 80, preferably 20 to 80, more preferably 20 to 70, mass % active ingredient of an additive or additives, being a para-alkyl-substituted diphenylamine of the invention as sole additives with one or more co-additives.

The oil of lubricating viscosity used in a concentrate is a suitable oleaginous, typically hydrocarbon, carrier fluid, e.g. mineral lubricating oil, or other suitable solvent. Oils of lubricating viscosity such as described herein, as well as aliphatic, naphthenic, and aromatic hydrocarbons, are examples of suitable carrier fluids for concentrates.

Concentrates constitute a convenient means of handling additives before their use, as well as facilitating solution or dispersion of additives in lubricating oil compositions. When preparing a lubricating oil composition that contains more than one type of additive (sometime referred to as "additive components"), each additive may be incorporated separately, each in the form of a concentrate. In many instances, however, it is convenient to provide a so-called additive "package" (also referred to as an "adpack") comprising one or more co-additives, such as described hereinafter, in a single concentrate.

The oil of lubricating viscosity may be provided in a major amount, in combination with a minor amount of at least one additive and, if necessary, one or more co-additives, such as described hereinafter, constituting a lubricating oil composition. This may be accomplished by adding the additive directly to the oil or by adding it in the form of a concentrate thereof to disperse or dissolve the additive. Additives may be added to the oil by methods known to those skilled in the art, either prior to, contemporaneously with, or subsequent to addition of other additives.

The terms "oil-soluble" or "oil-dispersible", or cognate terms, used herein do not necessarily indicate that the compounds or additives are soluble, dissolvable, miscible, or are capable of being suspended in the oil in all proportions. The compounds or additives are, however, soluble or stably dispersible in oil to an extent sufficient for them to exert their intended effect in the environment in which the oil is employed. Moreover, the additional incorporation of other additives may permit incorporation of higher levels of a particular additive, if desired.

The lubricating oil compositions may be used to lubricate mechanical engine components, particularly in internal combustion engines, e.g. spark-ignited or compression-ignited two- or four-stroke reciprocating engines, by adding the composition thereto. Preferably, they are crankcase lubricants.

The lubricating oil compositions and concentrates comprise defined components that may or may not remain the same chemically before and after mixing with an oleaginous carrier. This invention encompasses compositions and concentrates which comprise the defined components before mixing, or after mixing, or both before and after mixing.

When concentrates are used to make the lubricating oil compositions, they may for example be diluted with 3 to 100, e.g. 5 to 40, parts by mass of oil of lubricating viscosity per part by mass of the concentrate.

Co-Additives

The composition may include, as indicated above, one or more co-additives to provide certain performance characteristics. Examples of such co-additives are dispersants, detergents, metal rust inhibitors, viscosity index improvers, corrosion inhibitors, oxidation inhibitors, friction modifiers, anti-foaming agents, anti-wear agents and pour point depressants. Some are discussed in further detail below.

Ashless dispersants, which effectively reduce formation of deposits upon use in gasoline and diesel engines, when added to lubricating oils. Ashless dispersants useful in the compositions of the present invention comprises an oil soluble polymeric long chain backbone having functional groups capable of associating with particles to be dispersed. Typically, such dispersants comprise amine, alcohol, amide or ester polar moieties attached to the polymer backbone, often via a bridging group. The ashless dispersant may be, for example, selected from oil soluble salts, esters, amino-esters, amides, imides and oxazolines of long chain hydrocarbon-substituted mono- and polycarboxylic acids or anhydrides thereof; thiocarboxylate derivatives of long chain hydrocarbons; long chain aliphatic hydrocarbons having polyamine moieties attached directly thereto; and Mannich condensation products formed by condensing a long chain substituted phenol with formaldehyde and polyalkylene polyamine.

Preferably, the ashless dispersant is a "high molecular weight" dispersant having a number average molecular weight ($\overline{M}n$) greater than or equal to 4,000, such as between 4,000 and 20,000. The precise molecular weight ranges will depend on the type of polymer used to form the dispersant, the number of functional groups present, and the type of polar functional group employed. For example, for a polyisobutylene derivatized dispersant, a high molecular weight dispersant is one formed with a polymer backbone having a number average molecular weight of from about 1680 to about 5600. Typical commercially available polyisobutylene-based dispersants contain polyisobutylene polymers having a number average molecular weight ranging from about 900 to about 2300, functionalized by maleic anhydride (MW=98), and derivatized with polyamines having a molecular weight of from about 100 to about 350. Polymers of lower molecular weight may also be used to form high molecular weight dispersants by incorporating multiple polymer chains into the dispersant, which can be accomplished using methods that are know in the art.

Polymer molecular weight, specifically $\overline{M}_n$, can be determined by various known techniques. One convenient method is gel permeation chromatography (GPC), which additionally provides molecular weight distribution information (see W. W. Yau, J. J. Kirkland and D. D. Bly, "Modern Size Exclusion Liquid Chromatography", John Wiley and Sons, New York, 1979). If the molecular weight of an amine-containing dispersant (e.g., PIBSA-polyamine or PIBSA-PAM) is being determined, the presence of the amine may cause the dispersant to be adsorbed by the column, leading to an inaccurate molecular weight determination. Persons familiar with the operation of GPC equipment understand that this problem may be eliminated by using a mixed solvent system, such as tetrahydrofuran (THF) mixed with a minor amount of pyridine, as opposed to pure THF. The problem may also be addressed by capping the amine with acetic anhydride and correcting the molecular weight based on the number of capping groups. Another useful method for determining molecular weight, particularly for lower molecular weight polymers, is vapor pressure osmometry (see, e.g., ASTM D3592).

The degree of polymerization $D_p$ of a polymer is:

$$D_p = \sum_i \frac{Mn \times mol. \% \text{ monomer } i}{100 \times mol. \text{ wt monomer } i}$$

and thus for the copolymers of two monomers $D_p$ may be calculated as follows:

$$D_p = \frac{Mn \times mol. \% \text{ monomer } 1}{100 \times mol. \text{ wt monomer } 1} + \frac{Mn \times mol. \% \text{ monomer } 2}{100 \times mol. \text{ wt monomer } 2}$$

Preferably, the degree of polymerization for the polymer backbones used in the invention is at least 30, typically from 30 to 165, more preferably 35 to 100.

The preferred hydrocarbons or polymers employed in this invention include homopolymers, interpolymers or lower molecular weight hydrocarbons. One family of useful polymers comprise polymers of ethylene and/or at least one $C_3$ to $C_{28}$ alpha-olefin having the formula $H_2C=CHR^1$, wherein $R^1$ is straight or branched chain alkyl radical comprising 1 to 26 carbon atoms and wherein the polymer contains carbon-to-carbon unsaturation, preferably a high degree of terminal ethenylidene unsaturation. One preferred class of such polymers employed in this invention comprise interpolymers of ethylene and at least one alpha-olefin of the above formula, wherein $R^1$ is alkyl of from 1 to 18 carbon atoms, and more preferably is alkyl of from 1 to 8 carbon atoms, and more preferably still of from 1 to 2 carbon atoms. Therefore, useful alpha-olefin monomers and comonomers include, for example, propylene, butene-1, hexene-1, octene-1, 4-methyl-pentene-1, decene-1, dodecene-1, tridecene-1, tetradecene-1, pentadecene-1, hexadecene-1, heptadecene-1, octadecene-1, nonadecene-1, and mixtures thereof (e.g., mixtures of propylene and butene-1, and the like). Exemplary of such polymers are propylene homopolymers, butene-1 homopolymers, propylene-butene copolymers, ethylene-propylene copolymers, ethylene-butene-1 copolymers and the like, wherein the polymer contains at least some terminal and/or internal unsaturation. Preferred polymers are unsaturated copolymers of ethylene and propylene and ethylene and butene-1. The interpolymers of this invention may contain a minor amount, e.g. 0.5 to 5 mole % of a $C_4$ to $C_{18}$ non-conjugated diolefin comonomer. However, it is preferred that the polymers of this invention comprise only alpha-olefin homopolymers, interpolymers of alpha-olefin comonomers and interpolymers of ethylene and alpha-olefin comonomers. The molar ethylene content of the polymers employed in this invention is preferably in the range of 20 to 80%, and more preferably 30 to 70%. When propylene and/or butene-1 are employed as comonomer(s) with ethylene, the ethylene content of such copolymers is most preferably between 45 and 65%, although higher or lower ethylene contents may be present.

These polymers may be prepared by polymerizing alpha-olefin monomer, or mixtures of alpha-olefin monomers, or mixtures comprising ethylene and at least one $C_3$ to $C_{28}$ alpha-olefin monomer, in the presence of a catalyst system comprising at least one metallocene (e.g., a cyclopentadienyl-transition metal compound) and an alumoxane compound. Using this process, a polymer in which 95% or more of the polymer chains possess terminal ethenylidene-type unsaturation can be provided. The percentage of polymer chains exhibiting terminal ethenylidene unsaturation may be determined by FTIR spectroscopic analysis, titration, or $C^{13}$ NMR. Interpolymers of this latter type may be characterized by the formula POLY-C($R^1$)=$CH_2$ wherein $R^1$ is $C_1$ to $C_{26}$ alkyl, preferably $C_1$ to $C_{18}$ alkyl, more preferably $C_1$ to $C_8$ alkyl, and most preferably $C_1$ to $C_2$ alkyl, (e.g., methyl or ethyl) and wherein POLY represents the polymer chain. The chain length of the $R^1$ alkyl group will vary depending on the comonomer(s) selected for use in the polymerization. A minor amount of the polymer chains can contain terminal ethenyl, i.e., vinyl, unsaturation, i.e. POLY-CH=$CH_2$, and a portion of the polymers can contain internal monounsaturation, e.g. POLY-CH=CH=($R^1$), wherein $R^1$ is as defined above. These terminally unsaturated interpolymers may be prepared by known metallocene chemistry and may also be prepared as described in U.S. Pat. Nos. 5,498,809; 5,663,130; 5,705,577; 5,814,715; 6,022,929 and 6,030,930.

Another useful class of polymers is polymers prepared by cationic polymerization of isobutene, styrene, and the like. Common polymers from this class include polyisobutenes obtained by polymerization of a $C_4$ refinery stream having a butene content of about 35 to about 75% by wt., and an isobutene content of about 30 to about 60% by wt., in the presence of a Lewis acid catalyst, such as aluminum trichloride or boron trifluoride. A preferred source of monomer for making poly-n-butenes is petroleum feed streams such as Raffinate II. These feedstocks are disclosed in the art such as in U.S. Pat. No. 4,952,739. Polyisobutylene is a most preferred backbone of the present invention because it is readily available by cationic polymerization from butene streams (e.g., using $AlCl_3$ or $BF_3$ catalysts). Such polyisobutylenes generally contain residual unsaturation in amounts of about one ethylenic double bond per polymer chain, positioned along the chain.

As noted above, the polyisobutylene polymers employed are generally based on a hydrocarbon chain of from about 900 to 2,300. Methods for making polyisobutylene are known. Polyisobutylene can be functionalized by halogenation (e.g. chlorination), the thermal "ene" reaction, or by free radical grafting using a catalyst (e.g. peroxide), as described below.

Processes for reacting polymeric hydrocarbons with unsaturated carboxylic acids, anhydrides or esters and the preparation of derivatives from such compounds are disclosed in U.S. Pat. Nos. 3,087,936; 3,172,892; 3,215,707; 3,231,587; 3,272,746; 3,275,554; 3,381,022; 3,442,808; 3,565,804; 3,912,764; 4,110,349; 4,234,435; and GB-A-1,440,219. The polymer or hydrocarbon may be functionalized, for example, with carboxylic acid producing moieties (preferably acid or anhydride) by reacting the polymer or hydrocarbon under conditions that result in the addition of functional moieties or agents, i.e., acid, anhydride, ester moieties, etc., onto the polymer or hydrocarbon chains primarily at sites of carbon-to-carbon unsaturation (also referred to as ethylenic or olefinic unsaturation) using the halogen assisted functionalization (e.g. chlorination) process or the thermal "ene" reaction.

When using the free radical grafting process employing a catalyst (e.g. peroxide), the functionalization is randomly effected along the polymer chain. Selective functionalization can be accomplished by halogenating, e.g., chlorinating or brominating the unsaturated α-olefin polymer to about 1 to 8 wt. %, preferably 3 to 7 wt. % chlorine, or bromine, based on the weight of polymer or hydrocarbon, by passing the chlorine or bromine through the polymer at a temperature of 60 to 250° C., preferably 110 to 160° C., e.g., 120 to 140° C., for about 0.5 to 10, preferably 1 to 7 hours. The halogenated polymer or hydrocarbon (hereinafter backbones) can then be reacted with sufficient monounsaturated reactant capable of adding functional moieties to the backbone, e.g., monounsaturated carboxylic reactant, at 100 to 250° C., usually about 180° C. to 235° C., for about 0.5 to 10, e.g., 3 to 8 hours, such that the product obtained will contain the desired number of moles of the monounsaturated carboxylic reactant per mole of the halogenated backbones. Alternatively, the backbone and the monounsaturated carboxylic reactant can be mixed and heated while adding chlorine to the hot material.

The hydrocarbon or polymer backbone can be functionalized, e.g., with carboxylic acid producing moieties (preferably acid or anhydride moieties) selectively at sites of carbon-to-carbon unsaturation on the polymer or hydrocarbon chains, or randomly along chains using the three processes mentioned above, or combinations thereof, in any sequence.

The preferred monounsaturated reactants that are used to functionalize the backbone comprise mono- and dicarboxylic acid material, i.e., acid, anhydride, or acid ester material, including (i) monounsaturated $C_4$ to $C_{10}$ dicarboxylic acid wherein (a) the carboxyl groups are vicinyl, (i.e., located on adjacent carbon atoms) and (b) at least one, preferably both, of said adjacent carbon atoms are part of said mono unsaturation; (ii) derivatives of (i) such as anhydrides or $C_1$ to $C_5$ alcohol derived mono- or diesters of (i); (iii) monounsaturated $C_3$ to $C_{10}$ monocarboxylic acid wherein the carbon-carbon double bond is conjugated with the carboxy group, i.e., of the structure —C=C—CO—; and (iv) derivatives of (iii) such as $C_1$ to $C_5$ alcohol derived mono- or diesters of (iii). Mixtures of monounsaturated carboxylic materials (i)-(iv) also may be used. Upon reaction with the backbone, the monounsaturation of the monounsaturated carboxylic reactant becomes saturated. Thus, for example, maleic anhydride becomes backbone-substituted succinic anhydride, and acrylic acid becomes backbone-substituted propionic acid. Exemplary of such monounsaturated carboxylic reactants are fumaric acid, itaconic acid, maleic acid, maleic anhydride, chloromaleic acid, chloromaleic anhydride, acrylic acid, methacrylic acid, crotonic acid, cinnamic acid, and lower alkyl (e.g., $C_1$ to $C_4$ alkyl) acid esters of the foregoing, e.g., methyl maleate, ethyl fumarate, and methyl fumarate. The monounsaturated carboxylic reactant, preferably maleic anhydride, typically will be used in an amount ranging from about 0.01 to about 20 wt. %, preferably 0.5 to 10 wt. %, based on the weight of the polymer or hydrocarbon.

While chlorination normally helps increase the reactivity of starting olefin polymers with monounsaturated functionalizing reactant, it is not necessary with the polymers or hydrocarbons contemplated for use in the present invention, particularly those preferred polymers or hydrocarbons which possess a high terminal bond content and reactivity. Preferably, therefore, the backbone and the monounsaturated functionality reactant, e.g., carboxylic reactant, are contacted at elevated temperature to cause an initial thermal "ene" reaction to take place. Ene reactions are known.

The hydrocarbon or polymer backbone can be functionalized by random attachment of functional moieties along the polymer chains by a variety of methods. For example, the polymer, in solution or in solid form, may be grafted with the monounsaturated carboxylic reactant, as described above, in the presence of a free-radical initiator. When performed in solution, the grafting takes place at an elevated temperature in the range of about 100 to 260° C., preferably 120 to 240° C. Preferably, free-radical initiated grafting is accomplished in a mineral lubricating oil solution containing, for example, 1 to 50 wt. %, preferably 5 to 30 wt. % polymer based on the initial total oil solution.

The free-radical initiators that may be used are peroxides, hydroperoxides, and azo compounds, preferably those that have a boiling point greater than about 100° C. and decompose thermally within the grafting temperature range to provide free-radicals. Representative of these free-radical initiators are azobutyronitrile, bis-tertiary-butyl peroxide and dicumene peroxide. The initiator, when used, typically is used in an amount of between 0.005% and 1% by weight based on the weight of the reaction mixture solution. Typically, the aforesaid monounsaturated carboxylic reactant material and free-radical initiator are used in a weight ratio range of from about 1.0:1 to 30:1, preferably 3:1 to 6:1. The grafting is preferably carried out in an inert atmosphere, such as under nitrogen blanketing. The resulting grafted polymer is characterized by having carboxylic acid (or ester or anhydride) moieties randomly attached along the polymer chains: it being understood, of course, that some of the polymer chains remain ungrafted. The free radical grafting described above can be used for the other polymers and hydrocarbons of the present invention.

The functionalized oil-soluble polymeric hydrocarbon backbone can be characterized in terms of its functionality, which is the average number of moles of unsaturated carboxylic acids, anhydrides or ester reactant which have reacted per mole of polyalkene charged to the reaction, whether it has undergone functionalization or not. Functionality is based upon the saponification number ("SAP") of the product mixture and the $M_n$ of the polyalkene charged. SAP is the number of milligrams of KOH consumed in the complete neutralization of one gram of the resulting product mixture, and can be determined using ASTM D94.

The average number of succinic groups per mole of product mixture obtained when reacting maleic anhydride with polyalkene is determined using the following formula:

$$F = (SAP \times M_n)/((112,200 \times A.I.) - (SAP \times 98))$$

wherein SAP is the saponification number; $M_n$ is the number average molecular weight of the starting olefin polymer; AI is the percent active ingredient of the succinic-containing reaction product (the remainder being unreacted olefin polymer, maleic anhydride and diluent); and 98 is the molecular weight of maleic anhydride. Preferably, the starting olefin polymer is polyisobutylene having a number average molecular weight ranging from about 1500 to about 2500 and is derivatized with maleic anhydride such that the functionality, or succination ratio of the functionalized oil-soluble polymeric hydrocarbon backbone is from about 1.3 to 1.7 (e.g., 1.3 to 1.5).

The functionalized oil-soluble polymeric hydrocarbon backbone may then be further derivatized with a nucleophilic reactant, such as an amine, amino-alcohol, alcohol, metal compound, or mixture thereof, to form a corresponding derivative. Useful amine compounds for derivatizing functionalized polymers comprise at least one amine and can comprise one or more additional amine or other reactive or polar groups. These amines may be hydrocarbyl amines or may be predominantly hydrocarbyl amines in which the hydrocarbyl group includes other groups, e.g., hydroxy groups, alkoxy groups, amide groups, nitriles, imidazoline groups, and the like. Particularly useful amine compounds include mono- and polyamines, e.g., polyalkene and polyoxyalkylene polyamines of about 2 to 60, such as 2 to 40 (e.g., 3 to 20) total carbon atoms having about 1 to 12, such as 3 to 12, and preferably 3 to 9 nitrogen atoms per molecule. Mixtures of amine compounds may advantageously be used, such as those prepared by reaction of alkylene dihalide with ammonia. Preferred amines are aliphatic saturated amines, including, for example, 1,2-diaminoethane; 1,3-diaminopropane; 1,4-diaminobutane; 1,6-diaminohexane; polyethylene amines such as diethylene triamine; triethylene tetramine; tetraethylene pentamine; and polypropyleneamines such as 1,2-propylene diamine; and di-(1,2-propylene)triamine.

Other useful amine compounds include: alicyclic diamines such as 1,4-di(aminomethyl)cyclohexane and heterocyclic nitrogen compounds such as imidazolines. Another useful class of amines is the polyamido and related amido-amines as disclosed in U.S. Pat. Nos. 4,857,217; 4,956,107; 4,963,275; and 5,229,022. Also usable is tris(hydroxymethyl)amino methane (TAM) as described in U.S. Pat. Nos. 4,102,798; 4,113,639; 4,116,876; and UK 989,409.ABendrimers, star-like amines, and comb-structured amines may also be used. Similarly, one may use condensed amines, as described in U.S. Pat. No. 5,053,152. The functionalized polymer is reacted with the amine compound using conventional techniques as described, for example, in U.S. Pat. Nos. 4,234,435 and 5,229,022, as well as in EP-A-208,560.

The functionalized, oil-soluble polymeric hydrocarbon backbones may also be derivatized with hydroxy compounds such as monohydric and polyhydric alcohols, or with aromatic compounds such as phenols and naphthols. Preferred polyhydric alcohols include alkylene glycols in which the alkylene radical contains from 2 to 8 carbon atoms. Other useful polyhydric alcohols include glycerol, mono-oleate of glycerol, monostearate of glycerol, monomethyl ether of glycerol, pentaerythritol, dipentaerythritol, and mixtures thereof. An ester dispersant may also be derived from unsaturated alcohols, such as allyl alcohol, cinnamyl alcohol, propargyl alcohol, 1-cyclohexene-3-ol, and oleyl alcohol. Still other classes of alcohols capable of yielding ashless dispersants comprise ether-alcohols, including oxy-alkylene and oxy-arylene. Such ether-alcohols are exemplified by ether-alcohols having up to 150 oxy-alkylene radicals in which the alkylene radical contains from 1 to 8 carbon atoms. The ester dispersants may be di-esters of succinic acids or acid-esters, i.e., partially esterified succinic acids, as well as partially esterified polyhydric alcohols or phenols, i.e., esters having free alcohols or phenolic hydroxy radicals. An ester dispersant may be prepared by any one of several known methods as described, for example, in U.S. Pat. No. 3,381,022.

Preferred groups of dispersant include polyamine-derivatized poly α-olefin, dispersants, particularly ethylene/butene alpha-olefin and polyisobutylene-based dispersants. Particularly preferred are ashless dispersants derived from polyisobutylene substituted with succinic anhydride groups and reacted with polyethylene amines, e.g., polyethylene diamine, tetraethylene pentamine; or a polyoxyalkylene polyamine, e.g., polyoxypropylene diamine, trimethylolaminomethane; a hydroxy compound, e.g., pentaerythritol; and combinations thereof. One particularly preferred dispersant combination is a combination of (A) polyisobutylene substituted with succinic anhydride groups and reacted with (B) a hydroxy compound, e.g., pentaerythritol; (C) a polyoxyalkylene polyamine, e.g., polyoxypropylene diamine, or (D) a polyalkylene diamine, e.g., polyethylene diamine and tetraethylene pentamine using about 0.3 to about 2 moles of (B), (C) and/or (D) per mole of (A). Another preferred dispersant combination comprises a combination of (A) polyisobutenyl succinic anhydride with (B) a polyalkylene polyamine, e.g., tetraethylene pentamine, and (C) a polyhydric alcohol or polyhydroxy-substituted aliphatic primary amine, e.g., pentaerythritol or trismethylolaminomethane, as described in U.S. Pat. No. 3,632,511.

A particularly preferred dispersant composition is one comprising at least one polyalkenyl succinimide, which is the reaction product of a polyalkenyl substituted succinic anhydride (e.g., PIBSA), more preferably PIBSA (i) derived from PIB having $M_n$ of from about 1500 to about 2500 and (ii) a succination ratio of from about 1.3 to about 1.7; and a polyamine; which dispersant has a coupling ratio of from about 0.6 to about 1.25, preferably from about 0.6 to about 1.1, most preferably from about 0.6 to about 0.95. In the context of this disclosure, "coupling ratio" may be defined as a ratio of the number of succinyl groups in the PIBSA to the number of primary amine groups in the polyamine reactant.

Another class of ashless dispersants comprises Mannich base condensation products. Generally, these products are prepared by condensing about one mole of an alkyl-substituted mono- or polyhydroxy benzene with about 1 to 2.5 moles of carbonyl compounds) (e.g., formaldehyde and paraformaldehyde) and about 0.5 to 2 moles of polyalkylene polyamine, as disclosed, for example, in U.S. Pat. No. 3,442,808. Such Mannich base condensation products may include a polymer product of a metallocene catalyzed polymerization as a substituent on the benzene group, or may be reacted with a compound containing such a polymer substituted on a succinic anhydride in a manner similar to that described in U.S. Pat. No. 3,442,808, Examples of functionalized and/or derivatized olefin polymers synthesized using metallocene catalyst systems are described in the publications identified supra.

The dispersant can be further post treated by a variety of conventional post treatments such as boration, as generally taught in U.S. Pat. Nos. 3,087,936 and 3,254,025. Boration of the dispersant is readily accomplished by treating an acyl nitrogen-containing dispersant with a boron compound such as boron oxide, boron halide boron acids, and esters of boron acids, in an amount sufficient to provide from about 0.1 to about 20 atomic proportions of boron for each mole of acylated nitrogen composition. Useful dispersants contain from about 0.05 to about 2.0 mass %, e.g., from about 0.05 to about 0.7 mass % boron. The boron, which appears in the product as dehydrated boric acid polymers (primarily $(HBO_2)_3$), is believed to attach to the dispersant imides and diimides as amine salts, e.g., the metaborate salt of the diimide. Boration can be carried out by adding from about 0.5 to 4 mass %, e.g., from about 1 to about 3 mass % (based on the mass of acyl nitrogen compound) of a boron compound, preferably boric acid, usually as a slurry, to the acyl nitrogen compound and heating with stirring at from about 135° C. to about 190° C., e.g., 140° C. to 170° C., for from about 1 to about 5 hours, followed by nitrogen stripping. Alternatively, the boron treatment can be conducted by adding boric acid to a hot reaction mixture of the dicarboxylic acid material and amine, while removing water. Other post reaction processes commonly known in the art can also be applied.

The dispersant may also be further post treated by reaction with a so-called "capping agent". Conventionally, nitrogen-containing dispersants have been "capped" to reduce the adverse effect such dispersants have on the fluoroelastomer engine seals. Numerous capping agents and methods are known. Of the known "capping agents", those that convert basic dispersant amino groups to non-basic moieties (e.g., amido or imido groups) are most suitable. The reaction of a nitrogen-containing dispersant and alkyl acetoacetate (e.g., ethyl acetoacetate (EAA)) is described, for example, in U.S. Pat. Nos. 4,839,071; 4,839,072 and 4,579,675. The reaction of a nitrogen-containing dispersant and formic acid is described, for example, in U.S. Pat. No. 3,185,704. The reaction product of a nitrogen-containing dispersant and other suitable capping agents are described in U.S. Pat. Nos. 4,663,064 (glycolic acid); 4,612,132; 5,334,321; 5,356,552; 5,716,912; 5,849,676; 5,861,363 (alkyl and alkylene carbonates, e.g., ethylene carbonate); 5,328,622 (mono-epoxide); 5,026,495; 5,085,788; 5,259,906; 5,407,591 (poly (e.g., bis)-epoxides) and 4,686,054 (maleic anhydride or succinic anhydride). The foregoing list is not exhaustive and other methods of capping nitrogen-containing dispersants are known to those skilled in the art.

For adequate piston deposit control, a nitrogen-containing dispersant can be added in an amount providing the lubricating oil composition with from about 0.03 mass % to about 0.15 mass %, preferably from about 0.07 to about 0.12 mass %, of nitrogen.

Metal-containing or ash-forming detergents function both as detergents to reduce or remove deposits and as acid neutralizers or rust inhibitors, thereby reducing wear and corrosion and extending engine life. Detergents generally comprise a polar head with a long hydrophobic tail, with the polar head comprising a metal salt of an acidic organic compound. The salts may contain a substantially stoichiometric amount of the metal in which case they are usually described as normal or neutral salts, and would typically have a total base number or TBN (as can be measured by ASTM D2896) of from 0 to 80. A large amount of a metal base may be incorporated by reacting excess metal compound (e.g., an oxide or hydroxide) with an acidic gas (e.g., carbon dioxide). The resulting overbased detergent comprises neutralized detergent as the outer layer of a metal base (e.g. carbonate) micelle. Such overbased detergents may have a TBN of 150 or greater, and typically will have a TBN of from 250 to 450 or more.

Detergents that may be used include oil-soluble neutral and overbased sulfonates, phenates, sulfurized phenates, thiophosphonates, salicylates, and naphthenates and other oil-soluble carboxylates of a metal, particularly the alkali or alkaline earth metals, e.g., sodium, potassium, lithium, calcium, and magnesium. The most commonly used metals are calcium and magnesium, which may both be present in detergents used in a lubricant, and mixtures of calcium and/or magnesium with sodium, Particularly convenient metal detergents are neutral and overbased calcium sulfonates having TBN of from 20 to 450 TBN, and neutral and overbased calcium phenates and sulfurized phenates having TBN of from 50 to 450. Combinations of detergents, whether overbased or neutral or both, may be used.

Sulfonates may be prepared from sulfonic acids which are typically obtained by the sulfonation of alkyl substituted aromatic hydrocarbons such as those obtained from the fractionation of petroleum or by the alkylation of aromatic hydrocarbons. Examples included those obtained by alkylating benzene, toluene, xylene, naphthalene, diphenyl or their halogen derivatives such as chlorobenzene, chlorotoluene and chloronaphthalene. The alkylation may be carried out in the presence of a catalyst with alkylating agents having from about 3 to more than 70 carbon atoms. The alkaryl sulfonates usually contain from about 9 to about 80 or more carbon atoms, preferably from about 16 to about 60 carbon atoms per alkyl substituted aromatic moiety.

The oil soluble sulfonates or alkaryl sulfonic acids may be neutralized with oxides, hydroxides, alkoxides, carbonates, carboxylate, sulfides, hydrosulfides, nitrates, borates and ethers of the metal. The amount of metal compound is chosen having regard to the desired TBN of the final product but typically ranges from about 100 to 220 mass % (preferably at least 125 mass %) of that stoichiometrically required.

Metal salts of phenols and sulfurized phenols are prepared by reaction with an appropriate metal compound such as an oxide or hydroxide and neutral or overbased products may be obtained by methods well known in the art. Sulfurized phenols may be prepared by reacting a phenol with sulfur or a sulfur containing compound such as hydrogen sulfide, sulfur monohalide or sulfur dihalide, to form products which are generally mixtures of compounds in which 2 or more phenols are bridged by sulfur containing bridges.

Dihydrocarbyl dithiophosphate metal salts are frequently used as antiwear and antioxidant agents. The metal may be an alkali or alkaline earth metal, or aluminum, lead, tin, molybdenum, manganese, nickel or copper. The zinc salts are most commonly used in lubricating oil in amounts of 0.1 to 10, preferably 0.2 to 2 wt. %, based upon the total weight of the lubricating oil composition. They may be prepared in accordance with known techniques by first forming a dihydrocarbyl dithiophosphoric acid (DDPA), usually by reaction of one or more alcohol or a phenol with $P_2S_5$ and then neutralizing the formed DDPA with a zinc compound. For example, a dithiophosphoric acid may be made by reacting mixtures of primary and secondary alcohols. Alternatively, multiple dithiophosphoric acids can be prepared where the hydrocarbyl groups on one are entirely secondary in character and the hydrocarbyl groups on the others are entirely primary in character. To make the zinc salt, any basic or neutral zinc compound could be used but the oxides, hydroxides and carbonates are most generally employed. Commercial additives frequently contain an excess of zinc due to the use of an excess of the basic zinc compound in the neutralization reaction.

The preferred zinc dihydrocarbyl dithiophosphates are oil soluble salts of dihydrocarbyl dithiophosphoric acids and may be represented by the following formula:

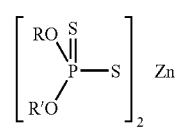

wherein R and R' may be the same or different hydrocarbyl radicals containing from 1 to 18, preferably 2 to 12, carbon atoms and including radicals such as alkyl, alkenyl, aryl, arylalkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, amyl, n-hexyl, i-hexyl, n-octyl, decyl, dodecyl, octadecyl, 2-ethylhexyl, phenyl, butylphenyl, cyclohexyl, methylcyclopentyl, propenyl, butenyl. In order to obtain oil solubility, the total number of carbon atoms (i.e. R and R') in the dithiophosphoric acid will generally be about 5 or greater. The zinc dihydrocarbyl dithiophosphate can therefore comprise zinc dialkyl dithiophosphates. The present invention may be particularly useful when used with lubricant compositions containing phosphorus levels of from about 0.02 to about 0.12 mass %, such as from about 0.03 to about 0.10 mass %, or from about 0.05 to about 0.08 mass %, based on the total mass of the composition. In one preferred embodiment, lubricating oil compositions of the present invention contain zinc dialkyl dithiophosphate derived predominantly (e.g., over 50 mol. %, such as over 60 mol. %) from secondary alcohols.

Supplemental oxidation inhibitors or antioxidants reduce the tendency of mineral oils to deteriorate in service. Oxidative deterioration can be evidenced by sludge in the lubricant, varnish-like deposits on the metal surfaces, and by viscosity growth. Such supplemental oxidation inhibitors include hindered phenols, diphenylamines other than the para-alkylated diphenylamines of the present invention, alkaline earth metal salts of alkylphenolthioesters having preferably $C_5$ to $C_{12}$ alkyl side chains, calcium nonylphenol sulfide, oil soluble phenates and sulfurized phenates, phosphosulfurized or sulfurized hydrocarbons, phosphorous esters, metal thiocarbamates, oil soluble copper compounds as described in U.S. Pat. No. 4,867,890, and molybdenum-containing compounds.

Representative examples of suitable viscosity modifiers are polyisobutylene, copolymers of ethylene and propylene, polymethacrylates, methacrylate copolymers, copolymers of an unsaturated dicarboxylic acid and a vinyl compound, interpolymers of styrene and acrylic esters, and partially hydrogenated copolymers of styrene/isoprene, styrene/butadiene, and isoprene/butadiene, as well as the partially hydrogenated homopolymers of butadiene and isoprene. Particularly preferred viscosity modifiers are star-shaped viscosity modifiers derived from hydrogenated polydiene arms, which viscosity modifiers have a shear stability index (SSI)≥35, more preferably, a star-shaped viscosity modifier comprising triblock arms derived from hydrogenated (polydiene-polystyrene-polydiene) and having an SSI≥45.

Friction modifiers and fuel economy agents that are compatible with the other ingredients of the final oil may also be included. Examples of such materials include glyceryl monoesters of higher fatty acids, for example, glyceryl monooleate; esters of long chain polycarboxylic acids with diols, for example, the butane diol ester of a dimerized unsaturated fatty acid; oxazoline compounds; and alkoxylated alkyl-substituted mono-amines, diamines and alkyl ether amines, for example, ethoxylated tallow amine and ethoxylated tallow ether amine.

Other known friction modifiers comprise oil-soluble organo-molybdenum compounds. Such organo-molybdenum friction modifiers also provide antioxidant and antiwear credits to a lubricating oil composition. Examples of such oil soluble organo-molybdenum compounds include dithiocarbamates, dithiophosphates, dithiophosphinates, xanthates, thioxanthates, sulfides, and the like, and mixtures thereof. Particularly preferred are molybdenum dithiocarbamates, dialkyldithiophosphates, alkyl xanthates and alkylthioxanthates.

Additionally, the molybdenum compound may be an acidic molybdenum compound. These compounds will react with a basic nitrogen compound as measured by ASTM test D-664 or D-2896 titration procedure and are typically hexavalent. Included are molybdic acid, ammonium molybdate, sodium molybdate, potassium molybdate, and other alkaline metal molybdates and other molybdenum salts, e.g., hydrogen sodium molybdate, $MoOCl_4$, $MoO_2Br_2$, $Mo_2O_3Cl_6$, molybdenum trioxide or similar acidic molybdenum compounds.

Among the molybdenum compounds useful in the compositions of this invention are organo-molybdenum compounds of the formula

and

wherein R is an organo group selected from the group consisting of alkyl, aryl, aralkyl and alkoxyalkyl, generally of from 1 to 30 carbon atoms, and preferably 2 to 12 carbon atoms and most preferably alkyl of 2 to 12 carbon atoms. Especially preferred are the dialkyldithiocarbamates of molybdenum.

Another group of organo-molybdenum compounds useful in the lubricating compositions of this invention are trinuclear molybdenum compounds, especially those of the formula $Mo_3S_kL_nQ_z$ and mixtures thereof wherein the L are independently selected ligands having organo groups with a sufficient number of carbon atoms to render the compound soluble or dispersible in the oil, n is from 1 to 4, k varies from 4 through 7, Q is selected from the group of neutral electron donating compounds such as water, amines, alcohols, phosphines, and ethers, and z ranges from 0 to 5 and includes non-stoichiometric values. At least 21 total carbon atoms should be present among all the ligand organo groups, such as at least 25, at least 30, or at least 35 carbon atoms.

A dispersant-viscosity index improver functions as both a viscosity index improver and as a dispersant. Examples of dispersant-viscosity index improvers include reaction products of amines, for example polyamines, with a hydrocarbyl-substituted mono- or dicarboxylic acid in which the hydrocarbyl substituent comprises a chain of sufficient length to impart viscosity index improving properties to the compounds. In general, the viscosity index improver dispersant may be, for example, a polymer of a $C_4$ to $C_{24}$ unsaturated ester of vinyl alcohol or a $C_3$ to $C_{10}$ unsaturated mono-carboxylic acid or a $C_4$ to $C_{10}$ di-carboxylic acid with an unsaturated nitrogen-containing monomer having 4 to 20 carbon atoms; a polymer of a $C_2$ to $C_{20}$ olefin with an unsaturated $C_3$ to $C_{10}$ mono- or di-carboxylic acid neutralized with an amine, hydroxylamine or an alcohol; or a polymer of ethylene with a $C_3$ to $C_{20}$ olefin further reacted either by grafting a $C_4$ to $C_{20}$ unsaturated nitrogen-containing monomer thereon or by grafting an unsaturated acid onto the polymer backbone and then reacting carboxylic acid groups of the grafted acid with an amine, hydroxy amine or alcohol.

Pour point depressants, otherwise known as lube oil flow improvers (LOFI), lower the minimum temperature at which the fluid will flow or can be poured. Such additives are well known. Typical of those additives that improve the low temperature fluidity of the fluid are $C_8$ to $C_{18}$ dialkyl fumarate/vinyl acetate copolymers, and polymethacrylates. Foam control can be provided by an antifoamant of the polysiloxane type, for example, silicone oil or polydimethyl siloxane.

Some of the above-mentioned additives can provide a multiplicity of effects; thus for example, a single additive may act as a dispersant-oxidation inhibitor. This approach is well known and need not be further elaborated herein.

Lubricating Oil Compositions

Multigrade lubricants perform over wide temperature ranges. Typically, they are identified by two numbers such as 10W-30 or 5W-30. The first number in the multigrade designation is associated with a safe cranking temperature (e.g., −20° C.) viscosity requirement for that multigrade oil as measured by a cold cranking simulator (CCS) under high shear rates (ASTM D5293). In general, lubricants that have low CCS viscosities allow the engine to crank more easily at lower temperatures and thus improve engine startability at those ambient temperatures.

The second number in the multigrade designation is associated with a lubricant's viscosity under normal operating temperatures and is measured in terms of the kinematic viscosity (kV) at 100° C. (ASTM D445). The high temperature viscosity requirement brackets minimum and maximum kinematic viscosity at 100° C. Viscosity at high temperatures is desirable to prevent engine wear that would result if the lubricant thinned out too much during engine operation. However the lubricant should not be too viscous because excessive viscosity may cause unnecessary viscous drag and work to pump the lubricant which in turn can increase fuel consumption. In general, the lower a lubricants' $kV_{100}$, the better the scores that lubricant achieves in fuel economy tests.

Thus, in order to qualify for a given multigrade oil designation a particular multigrade oil must simultaneously meet both strict low and high temperature viscosity requirements that are set by SAE specifications such as SAE J300. The current viscosity limits set in SAE J300 are as follows:

SAE VISCOSITY GRADES

| SAE viscosity grade | Maximum CCS Viscosity ($10^{-3}$ Pa·s @ (° C.)) | $kV_{100° C.}$ (mm²/s) minimum | $kV_{100° C.}$ (mm²/s) maximum |
|---|---|---|---|
| 0 W | 3250 (−30) | 3.8 | — |
| 5 W | 3500 (−25) | 3.8 | — |
| 10 W | 3500 (−20) | 4.1 | — |
| 15 W | 3500 (−15) | 5.6 | — |
| 20 W | 4500 (−10) | 5.6 | — |
| 25 W | 6000 (−5) | 9.3 | — |
| 20 | — | 5.6 | <9.3 |
| 30 | — | 9.3 | <12.5 |
| 40 | — | 12.5 | <16.3 |
| 50 | — | 16.3 | <21.9 |
| 60 | — | 21.9 | <26.1 |

In the SAE J300 scheme multigrade oils meet the requirements of both low temperature and high temperature performance. For example, an SAE 5W-30 multigrade oil has viscosity characteristics that satisfy both the 5W and the 30 viscosity grade requirements—i.e., a maximum CCS viscosity of 3500×$10^{-3}$ Pa·s at −25° C., a minimum $kV_{100° C.}$ of 9.3 mm²/s and a maximum $kV_{100}$ of <12.5 mm²/s.

The viscosity characteristics of a lubricant depend primarily on the viscosity characteristics of the base stock, the viscosity characteristics of the viscosity modifier; and the viscosity characteristics of the high molecular weight dispersants. SAE 0W and SAE 5W multigrade crankcase lubricants having $kV_{100}$ of 12.5 mm²/s or less, particularly 9.3 mm²/s or less, more particularly SAE≤0W multigrade crankcase lubricants having $kV_{100}$ of 12.5 mm²/s or less, particularly 9.3 mm²/s or less, most particularly less than 9.3 mm²/s (a SAE≤0W≤20) multigrade crankcase lubricants that provide good deposit control (WPD) and sludge control (Sequence VD) would be particularly hard to blend without means to reduce polymer content associated with the content of high molecular weight dispersant. Because the para-alkylated diphenylamines of the present invention provide a low molecular weight option for providing good piston deposit control, and therefore allow for a reduction in the amount of high molecular weight dispersant, the para-alkylated diphenylamines of the present invention are particularly well suited for the formulation of such low and ultra-low viscosity multigrade lubricating oil compositions.

Preferably these low and ultra-low viscosity multigrade lubricating oil compositions comprise the para-alkylated diphenylamines of the present invention in combination with a dispersant providing a high degree of performance at minimum polymer content, such as a polyalkenyl succinimide, which is the reaction product of a polyalkenyl substituted succinic anhydride (e.g., PIBSA), more preferably PIBSA (i) derived from PIB having $M_n$ of from about 1500 to about 2500 and (ii) a succination ratio of from about 1.3 to about 1.7; and a polyamine; which dispersant has a coupling ratio of from about 0.6 to about 1.25, preferably from about 0.6 to about 1.1, most preferably from about 0.6 to about 0.95; preferably in an amount providing the lubricating oil composition with ≤2 mass %, such as ≤1.5 mass %, more preferably ≤1 mass % of dispersant polymer and/or a viscosity modifier providing a high degree of performance at minimum polymer content, such as a star-shaped viscosity modifier derived from hydrogenated polydiene arms, which viscosity modifiers have a shear stability index (SSI)≥35, more preferably, a star-shaped viscosity modifier comprising triblock arms derived from hydrogenated (polydiene-polystyrene-polydiene) and having an SSI≥45. Preferably, these lubricating oil compositions further comprise a minor amount of a phenolic antioxidant.

Engine

The invention is applicable to a range of internal combustion engines such as compression-ignited and spark-ignited two- or four-cylinder reciprocating engines. Examples include engines for passenger ears, light commercial vehicles and heavy duty on-highway trucks; engines for aviation, power-generation, locomotive and marine equipment; and heavy duty off-highway engines such as may be used for agriculture, construction and mixing.

EXAMPLES

This invention will now be particularly described in the following examples which are not intended to limit the scope of the claims hereof.

Alkylated Diphenylamines ("DPA's")

The following alkylated DPA's were blended into formulations, which were then tested as described below:

"$C_{15}$ DPA mono": a predominantly mono-para-alkylated DPA, predominating in propene-pentamer ($C_{15}$) derived alkyl groups "$C_{15}$ DPA di": a predominantly di-para-alkylated DPA, predominating in propene-pentamer ($C_{15}$) derived alkyl groups "$C_{12}$ DPA mono": a predominantly mono-para-alkylated DPA, predominating in propene-tetramer ($C_{12}$) derived alkyl groups "$C_9$ DPA": a predominantly di-para-alkylated DPA, predominating in propene-trimer ($C_9$) derived alkyl groups.

As an illustration of a method of making the above DPA's, the following example for making "$C_{15}$ DPA mono" is provided:

Diphenylamine (169 g; 1.00 mol), aluminium trichloride (16.9 g, 10% w/w) and a $C_{15}$ oligomeric propene-based olefin stream (210 g; 1.00 mol) were added to a 2 litre 5 necked round-bottomed flask. The reaction contents were heated to 190° C. under nitrogen, stirring at 500 rpm for 6 hours at this temperature. The reactor was cooled to 60° C. and the product removed and treated with sodium hydroxide (120 g, 10% solution). The resulting mixture was washed twice with 100 g water, and the organic layer separated. Any remaining water and olefin was removed on a rotovap under vacuum, to give an alkyl-substituted diphenylamine as a brown oil, where the alkyl group was predominantly mono-substituted $C_{15}$. Before the removal of the unreacted diphenylamine the reaction mixture consisted of 54.03% diphenylamine, 38.78% mono-alkylated diphenylamine and 7.19% di-alkylated diphenylamine by HPLC. After the diphenylamine had been removed the product consisted of 84% mono-alkylated diphenylamine and 16% di alkylated diphenylamine, the substitution(s) being in the para position(s).

The olefin stream used, analysed by GC-field ionisation mass spectrometry ("FIMS"), contained 53.15% $C_{15}$ and 13.80% $C_{18}$ olefins together with other olefins in individual proportions of less than 10%.

The "$C_{15}$ DPA di" and "$C_{12}$ DPA mono" were made by analogous methods. "$C_9$ DPA" was a commercially-available material.

Formulations and Testing
Sequence IIIG Testing (ASTM D7320)

The above DPA's were each formulated into petrol car crankcase lubricants in combination with one or more hindered phenol antioxidants, anti-wear additives, ashless dispersants, metal detergents, friction modifiers, Mo-based additives and viscosity modifiers.

The lubricants were subjected to Sequence IIIG Testing; the results obtained are set out in the table below:

| Form. | DPA (wt %) | hindered phenol wt % | Dispersant wt % | PVIS | WPD | ACLW |
|---|---|---|---|---|---|---|
| 1 | $C_9$ DPA (0.9) | 0.2 | 4 | 132.3 | 3.3* | 35.4 |
| 2 | $C_9$ DPA (1) | 0 | 4.2 | 389.9* | 3.35* | 18.5 |
| 3 | $C_{15}$ DPA mono (1.5) | 0.25 | 4.2 | 107.3 | 4.36 | 39.6 |
| 4 | $C_{15}$ DPA di (2.1) | 0.25 | 4.2 | 104.7 | 4.17 | 53.4 |
| 5 | $C_{12}$ DPA mono (1.5) | 0.25 | 4.2 | 106.3 | 4.12 | 47.2 |

Key to test:
PVIS kinematic viscosity increase (150% maximum to pass)
WPD weighted piston deposits (3.5 merits minimum to pass)
ACLW average cam lifter wear (60 microns maximum to pass)
*failing result.

The lubricants were identical other than as indicated in the table. Formulations 3 and 4 contained the same % N from the DPA. $C_9$ DPA is known to be adverse for the WPD test; it is therefore surprising that Formulations 3-5, which have higher treat rates of aminic anti-oxidant and would therefore be expected to have poorer WPD performance, pass the WPD test. The results also show general superiority for the $C_{15}$ DPA-containing formulations, wherein mono is better than di because the weight percentage treat rate of di- must be increased in order to provide the same performance as mono-.

Formulations 1 and 2 show that formulations containing $C_9$ alkylated diphenylamine at 0.9% and 1% cannot pass MG weighted piston deposits (WPD) with dispersant treats of 4-4.2%. In contrast, Formulation 3, with 1.5% treat of $C_{15}$ DPA, shows improved passing IIIG WPD merit ratings with the same amount of dispersant. Although hindered phenol can improve IIIG WPD merits, engine test modelling shows that the 0.25% treat present in formulations 3, 4 and 5, is insufficient to give a significant improvement in IIIG WPD merits and may be discounted when comparing the IIIG WPD merit figures.

Sequence VG Testing (ASTM D5302)

The following DPA's, namely $C_{15}$ DPA mono, $C_{12}$ DPA mono and $C_9$ DPA, were each formulated into petrol car crankcase lubricants in combination with one or more hindered phenol antioxidants, anti-wear additives, ashless dispersants, metal detergents, friction modifiers, Mo-based additives and viscosity modifiers. The lubricants were subjected to Sequence MG Testing; the results are set out in the table below:

| Form. | DPA (wt %) | hindered phenol wt % | Dispersant wt % | AES | AEV | APV | RCS |
|---|---|---|---|---|---|---|---|
| 6 | $C_9$ DPA (0.7) | 0.5 | 3.6 | 7.05* | 8.86* | 7.37* | 8.82 |
| 7 | $C_{15}$ DPA mono (0.7) | 0.5 | 3.6 | 8.4 | 9.3 | 8.3 | 9.36 |
| 8 | $C_{15}$ DPA mono (1.5) | 0 | 4.2 | 9.53 | 9.35 | 8.4 | 9.58 |
| 9 | $C_{12}$ DPA mono (1.5) | 0 | 4.2 | 7.84 | 9.14 | 8.11 | 9.57 |

Key to test:
AES average engine sludge (7.5 merits minimum to pass)
AEV average engine varnish (8.9 merits minimum to pass)
APV average piston varnish (7.5 merits minimum to pass)
RCS rocker cover sludge (8.0 merits minimum to pass)
*failing result.

The lubricants were identical other than as indicated in the table. $C_9$ DPA is known to be deleterious in the AES test; it is therefore surprising the $C_{15}$ DPA mono gives a better performance in that test (cf. Formulations 6 and 7). Also, $C_{15}$ DPA mono gives a better performance than $C_{12}$ DPA mono in the AES, AEV, and APV tests (cf. Formulations 8 and 9).

Comparing Formulations 6 and 7 shows that $C_{15}$ DPA is better than $C_9$ alkylated DPA in terms of all Sequence VG test parameters.

Comparing Formulations 8 and 9 shows that $C_{15}$ DPA is better than $C_{12}$ DPA in terms of AES, AEV and APV.

Oxidation Testing $C_{15}$ DPA mono and $C_9$ DPA were each formulated into petrol car crankcase lubricants in combination with one or more hindered phenol antioxidants, anti-wear additives, ashless dispersants, metal detergents, friction modifiers and Mo-based additives.

Two sets of lubricants were formulated: each member of the first set contained 1.5 mass % of $C_{15}$ DPA mono or $C_9$ DPA, and 75 ppm by mass of Mo; each member of the second set contained 0.7 mass % of $C_{15}$ DPA mono or of $C_9$ DPA, and 200 ppm by mass of Mo. All lubricants were otherwise identical.

Each of the four lubricants was subjected to ASTM D7097, a "Moderately High Temperature Thermo-Oxidation Engine Oil Simulation" Test or MHT TEOST. The results are set out in the table below:

| Formulation | DPA (wt %) | Mo ppm | Deposit mg | repeatability* mg |
|---|---|---|---|---|
| 10 | $C_9$ DPA (1.5) | 75 | 24.37 | 6 |
| 11 | $C_{15}$ DPA mono (1.5) | 75 | 29.77 | 6.8 |

-continued

| Formulation | DPA (wt %) | Mo ppm | Deposit mg | repeatability* mg |
|---|---|---|---|---|
| 12 | $C_9$ DPA (0.7) | 200 | 36 | 7.8 |
| 13 | $C_{15}$ DPA mono (1.5) | 200 | 19 | 5.25 |

*calculated from the ASTM standard.

The results are expressed in terms of mg of deposit produced: a lower value indicates a better anti-oxidancy performance, account being taken of repeatability when comparing results.

Formulation 11 exhibits a comparable anti-oxidancy performance to that of the Formulation 10.

Formulation 13 exhibits a better anti-oxidancy performance than Formulation 12.

The results are surprising, however, because the $C_{15}$ DPA mono has a higher molecular weight than $C_9$ DPA. It therefore has a lower percentage of amine nitrogen and therefore, at the same treat rate, would be expected to give rise to a poorer anti-oxidancy performance.

The invention claimed is:

1. A method of preparing a para-alkyl-substituted diphenylamine comprising catalytically alkylating diphenylamine with an alkylating agent in the form of a mixture of branched-chain propene oligomers, wherein greater than 50% of the oligomer that is present is $C_{15}$ oligomer, and oligomers having 9 or fewer carbon atoms and oligomers having from 24 or more carbon atoms constitute 10% or less of the mixture, all percentages being area/area as measured chromatographically; and wherein the mole ratio of alkylating agent to diphenylamine is in the range of 1:3 to 1.5:1.

2. A method as claimed in claim 1 wherein said mixture of branched-chain alkene-oligomers is a mixture of propene oligomers.

* * * * *